United States Patent
Pullagurla et al.

(10) Patent No.: US 11,274,164 B2
(45) Date of Patent: Mar. 15, 2022

(54) METHOD FOR THE PREPARATION OF SULFOBUTYLETHER BETA CYCLODEXTRIN SODIUM

(71) Applicant: BIOPHORE INDIA PHARMACEUTICALS PVT. LTD., Hyderabad (IN)

(72) Inventors: Manik Reddy Pullagurla, Hyderabad (IN); Bhaskar Reddy Pitta, Hyderabad (IN); Suresh Babu Namana, Hyderabad (IN); Radha Nagarapu, Hyderabad (IN); Jagadeesh Babu Rangisetty, Hyderabad (IN)

(73) Assignee: BIOPHORE INDIA PHARMACEUTICALS PVT. LTD., Hyderabad (IN)

( * ) Notice: Subject to any disclaimer, the term of this patent is extended or adjusted under 35 U.S.C. 154(b) by 0 days.

(21) Appl. No.: 16/484,023

(22) PCT Filed: Feb. 7, 2018

(86) PCT No.: PCT/IN2018/050063
§ 371 (c)(1),
(2) Date: Aug. 6, 2019

(87) PCT Pub. No.: WO2018/146698
PCT Pub. Date: Aug. 16, 2018

(65) Prior Publication Data
US 2020/0095343 A1 Mar. 26, 2020

(30) Foreign Application Priority Data
Feb. 7, 2017 (IN) .............................. 201741004493

(51) Int. Cl.
*C08B 37/16* (2006.01)
*C08L 5/16* (2006.01)

(52) U.S. Cl.
CPC ............ *C08B 37/0012* (2013.01); *C08L 5/16* (2013.01)

(58) Field of Classification Search
None
See application file for complete search history.

(56) References Cited

U.S. PATENT DOCUMENTS

| 5,376,645 | A | 12/1994 | Stella et al. |
| 6,153,746 | A | 11/2000 | Shah et al. |
| 2009/0012042 | A1 | 1/2009 | Ren et al. |
| 2010/0093663 | A1* | 4/2010 | Antle ..................... A61K 31/58 514/58 |
| 2015/0025023 | A1 | 1/2015 | Savage et al. |

OTHER PUBLICATIONS

Puskás, (2015). Sulfobutylether-cyclodextrins: Structure, degree of substitution and functional performance. (Year: 2015).*
Millipore, Application Note, Endotoxin Removal, The Solution With Membrane Separation Technology, 2012. (Year: 2012).*
Dr. Welder, Extraction, internet article, https://web.archive.org/web/20151016130718/https://www.dartmouth.edu/~welderco/extraction/indexextract.html, published 2015. (Year: 2015).*
International Search Report for PCT/IN2018/050063 dated Apr. 25, 2018.

* cited by examiner

*Primary Examiner* — Layla D Berry
(74) *Attorney, Agent, or Firm* — McCormick, Paulding & Huber PLLC

(57) ABSTRACT

The present invention relates to an improved method for the synthesis of sulfobutylether beta cyclodextrin sodium and to provide an amorphous form of sulfobutylether beta cyclodextrin sodium having a 1,4-butane sultone content less than 0.5 ppm. The present invention further provides sulfobutylether beta cyclodextrin sodium containing less than 35 IU/g of Bacterial endotoxins.

9 Claims, 1 Drawing Sheet

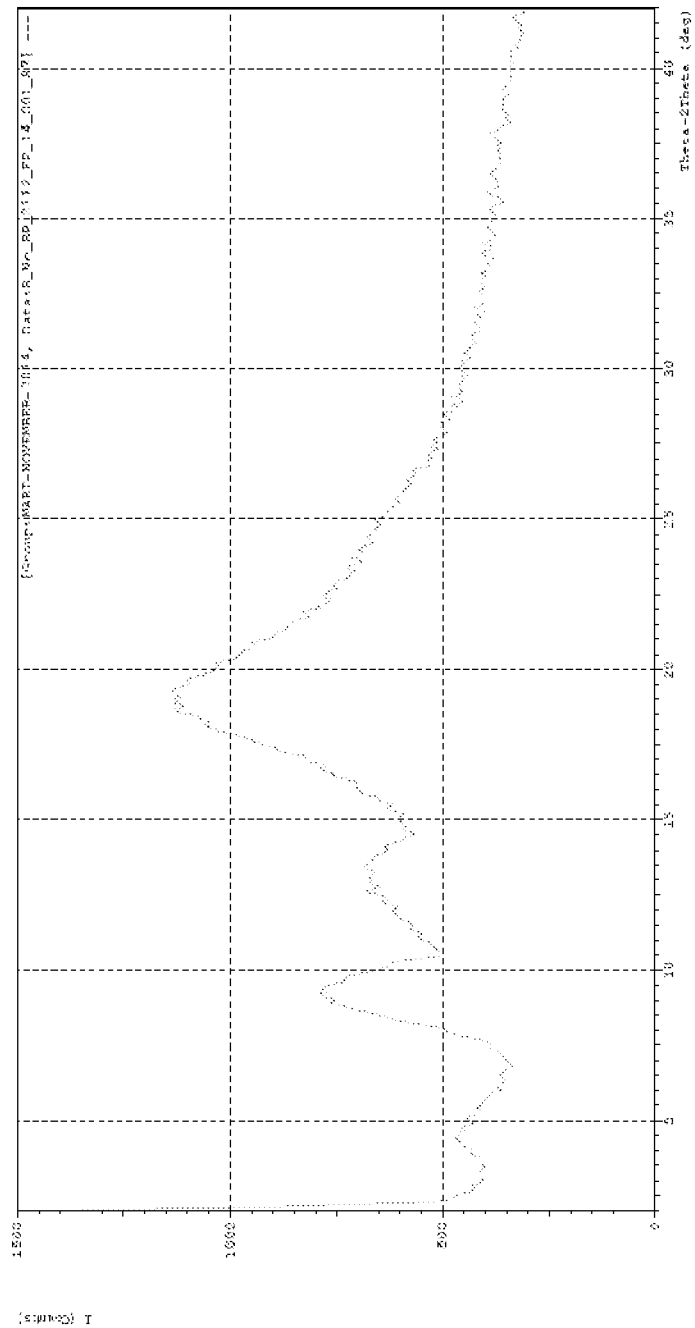
X-Ray diffraction pattern of sulfobutylether beta cyclodextrin sodium (I)

METHOD FOR THE PREPARATION OF SULFOBUTYLETHER BETA CYCLODEXTRIN SODIUM

CROSS-REFERENCE TO RELATED PATENT APPLICATION(S)

This application is a National Stage application of International Patent Application No. PCT/IN2018/050063, filed on Feb. 7, 2018, which claim priority to Indian Patent Application No. 201741004493 filed on Feb. 7, 2017; the disclosures of which are incorporated herein by reference.

The present invention describes a novel process for the preparation of pharmaceutical grade sulfobutylether beta cyclodextrin sodium (I) which is being used as an excipient in multiple drugs. Sulfobutylether beta cyclodextrin sodium is modified form of beta cyclodextrin comprising varying degrees of substitutions.

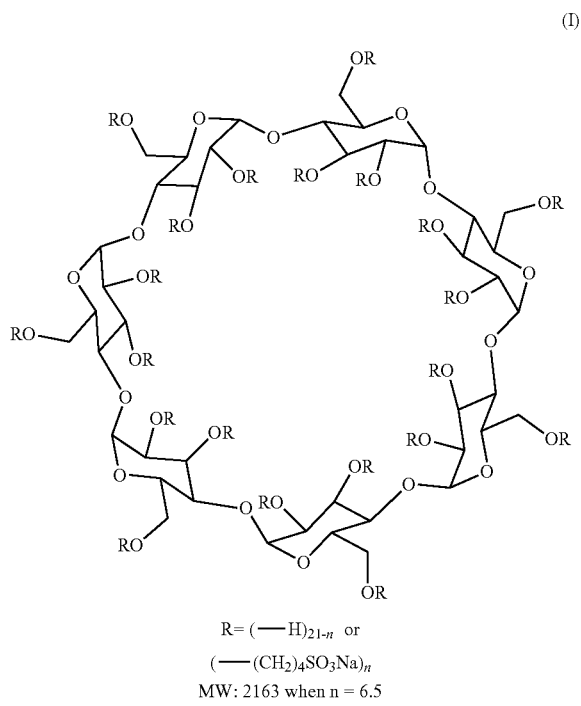

R= (—H)$_{21-n}$ or
(—(CH$_2$)$_4$SO$_3$Na)$_n$
MW: 2163 when n = 6.5

BACKGROUND

Sulfobutylether beta cyclodextrin sodium also known as beta cyclodextrin sulfobutyl ether sodium, is being used as an excipient in most of the drug formulations. Sodium salt of sulfobutylether beta cyclodextrin enhances the solubility of the drug.

The following patents and applications describe the synthesis of sulfobutylether beta cyclodextrin sodium (I). U.S. Pat. No. 5,376,645 described a general method for the production of cyclodextrin derivatives which included i) dissolving the cyclodextrin in aqueous base, ii) reacting with an amount of an appropriate alkyl sultone, corresponding to the number of moles of primary CD hydroxyl group present, iii) dilution of the reaction mixture with water & neutralization with hydrochloric acid, iv) purification of the reaction mass by dialysis followed by concentration of the solution by ultrafiltration, v) ion-exchange chromatography of the concentrated solution to remove unreacted cyclodextrin, and vi) freeze drying to give the final product.

U.S. Pat. No. 6,153,746 covered a method for the synthesis of SBECD (sulfobutylether beta cyclodextrin sodium), which involved reacting an unsubstituted cyclodextrin with an alkyl sultone in presence of base. Specifically, in this process the base was added in a stepwise manner and pH was controlled between 8-11 until residual unreacted cyclodextrin was less than 0.5%. Additional amount of base was also added to achieve the required degree of substitution, and to destroy the residual alkyl sultone.

US2015/0025023 discusses a method for the preparation of sulphoalkyl ether-cyclodextrin, by reacting cyclodextrin with a base to form activated cyclodextrin, and then separately contacting the activated cyclodextrin with an alkyl sultone to form sulphoalkyl ether-cyclodextrin. In this patent the activation reaction was carried out in batch and the sulphoalkylation reaction carried out under continuous flow conditions.

One primary constraint in all the literature reported so far was the use of excess amount of toxic 1,4-butane sultone relative to the desired average degree of substitution of the corresponding cyclodextrin derivative. Consequently, this 1,4-butane sultone remained in the final cyclodextrin derivative. Typically, the residual butane sultone could be destroyed at higher temperature by employing excess base, but that would lead to predominantly more coloration of the product along with the formation of high amount of degradation impurities which included hydroxyl butane-1-sulfonic acid, Bis(4-sulfobutyl) ether and other ring opening polymerization products.

The second major issue was controlling or elimination of bacterial endotoxins in the final sulfobutylether beta cyclodextrin sodium (SBECD) which was isolated from the aqueous solution that was usually contaminated with bacterial endotoxins. The procedures described in literature do not provide a process for removal of bacterial endotoxins. Hence, there is a need to provide an improved process for the manufacturing of sulfobutylether beta cyclodextrin sodium (SBECD), which addresses the issues associated with the prior art processes.

SUMMARY

In light of the forgoing deficiencies in the prior art, one of the object of the invention is to provide pharmaceutical grade sulfobutylether beta cyclodextrin sodium of formula (I).

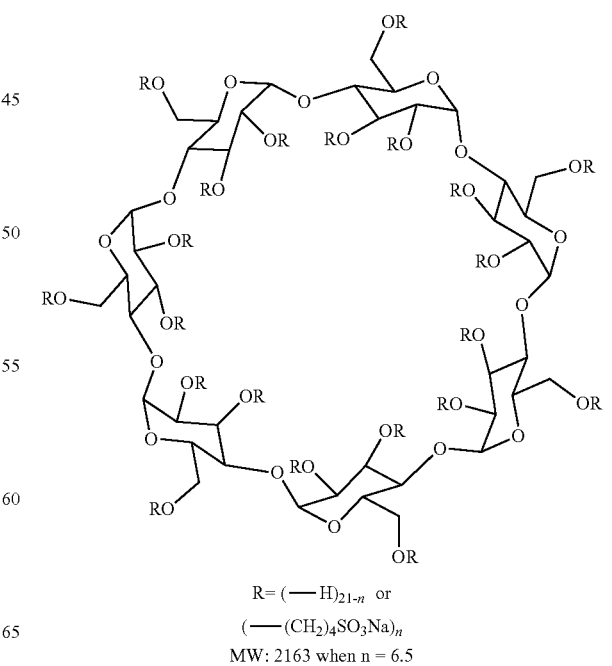

R= (—H)$_{21-n}$ or
(—(CH$_2$)$_4$SO$_3$Na)$_n$
MW: 2163 when n = 6.5

Another object of the invention is to develop an improved process for the synthesis of pharmaceutical grade sulfobutylether beta cyclodextrin sodium (I) having 1,4-butane sultone content less than 0.5 ppm.

Yet another object of the invention is to provide an alternate method for the preparation of amorphous form of sulfobutylether beta cyclodextrin sodium (I) with substantially lesser amounts of BET, i.e. less than 35 IU/g of bacterial endotoxins, preferably less than 10 IU/g of bacterial endotoxins or more preferably free of bacterial endotoxins.

Another object of the invention is to provide sulfobutylether beta cyclodextrin sodium (I) which has bulk density greater than 0.67 g/cm$^3$; and tap density greater than 0.76 g/cm$^3$.

The present invention provides an improved process for the preparation of sulfobutylether beta cyclodextrin sodium of formula (I), the said process comprising the steps of:
a. treating beta-cyclodextrin with an aqueous base to form activated beta-cyclodextrin;
b. reacting the activated cyclodextrin with an appropriate quantity of 1,4-butane sultone;
c. adjusting pH of the reaction mass to 6-6.5 using aqueous hydrochloric acid and removing coloured impurities by the process comprising treatment with neutral charcoal, stirring and filtering the reaction mass under vacuum through Hyflo at 25-30° C.;
d. removing the unreacted 1,4-butane sultone by a process comprising washing the reaction mass with an organic solvent and separating the aqueous and organic layers followed by ultrafiltration by employing 1.0 KD membrane;
e. treating the retentate with neutral charcoal and again passing through ultrafiltration using 10 KD membrane system to eliminate bacterial endotoxins; and
f. the aqueous solution of sulfobutylether beta cyclodextrin sodium was freeze dried by lyophilization to produce sulfobutylether beta cyclodextrin sodium (I);
wherein the characteristics of sulfobutylether beta cyclodextrin sodium (I) obtained comprises of:
i. UV absorbance in the range of 245 nm to 270 nm and 320 nm to 350 nm at 500 mg/mL concentration is greater than 0.5 A. U,
ii. UV absorbance in the range of 245 nm to 270 nm and 320 nm to 350 nm at 300 mg/mL concentration is greater than 1.0 A. U,
iii. Bulk density greater than 0.67 g/cm$^3$,
iv. Tap density greater than 0.76 g/cm$^3$,
v. 1,4-butane sultone content less than 0.5 ppm or
vi. having BET (Bacterial endotoxins) less than 10 IU/g.

In some embodiment of the invention, the aqueous base used in step a) of the above described process for the preparation of sulfobutylether beta cyclodextrin sodium (I) is selected from sodium hydroxide or sodium bicarbonate.

In some embodiment of the invention, the quantity of 1,4-butane sultone used in step b) of the above described process for the preparation of sulfobutylether beta cyclodextrin sodium (I)) is in between 7-9.5 equivalents.

In some embodiment of the invention, the organic solvent used in step d) of the above described process for the preparation of sulfobutylether beta cyclodextrin sodium (I) is selected from the group comprising of dichloromethane, ethyl acetate, methylene chloride, diethyl ether or methyl tert-butyl ether.

In some embodiment of the invention, there is provided a process for the preparation of sulfobutylether beta cyclodextrin sodium (I), wherein the obtained sulfobutylether beta cyclodextrin sodium comprises less than 0.5% (w/w) of unreacted beta cyclodextrin.

In some embodiment of the invention, there is provided a process for the preparation of sulfobutylether beta cyclodextrin sodium (I), wherein the obtained sulfobutylether beta cyclodextrin sodium has average degree of substitution of 6.2 to 6.9.

In some embodiment of the invention, there is provided a process for the preparation of sulfobutylether beta cyclodextrin sodium (I) having bacterial endotoxins less than 10 IU/g, the said process comprising the steps of:
a. purifying crude aqueous sulfobutylether beta cyclodextrin sodium by ultrafiltration using 700 Dalton to 1.0 KD membrane;
b. concentrating the aqueous layer to 15-30% of (w/v) by vacuum distillation;
c. passing the concentrated aqueous sulfobutylether beta cyclodextrin sodium through 10 KD membrane in ultrafiltration; and
d. lyophilization of aqueous sulfobutylether beta cyclodextrin sodium (I) obtained in step (c) to obtain sulfobutylether beta cyclodextrin sodium (I) having bacterial endotoxins less than 10 IU/g.

BRIEF DESCRIPTION OF DRAWINGS

The following drawings, illustrate the specific embodiments of the invention, but should not be construed as restricting the scope of the invention in anyway.

FIG. 1 is an X-Ray diffraction pattern of sulfobutylether beta cyclodextrin sodium.

DETAILED DESCRIPTION

In one embodiment, this invention provides an alternate method for the synthesis of sulfobutylether beta cyclodextrin sodium (I),

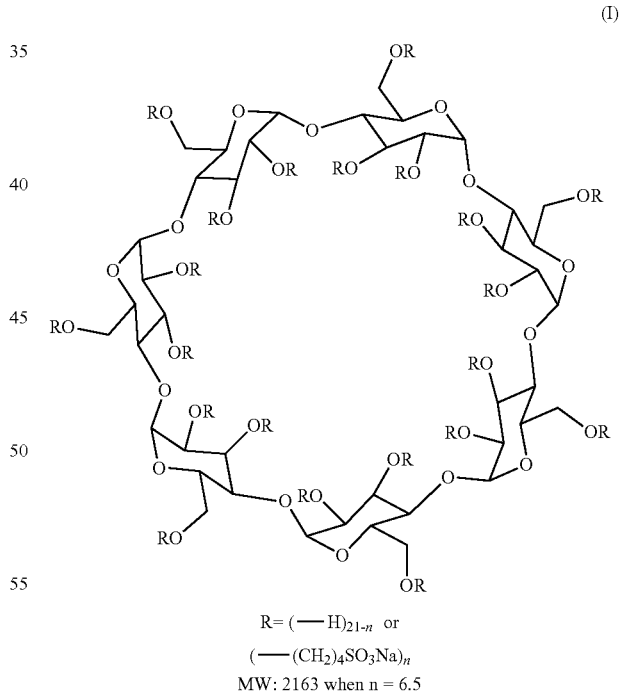

R= (—H)$_{21-n}$ or
(—(CH$_2$)$_4$SO$_3$Na)$_n$
MW: 2163 when n = 6.5 the said process comprising the steps of:
a. treating beta-cyclodextrin with an aqueous base to form activated beta-cyclodextrin;
b. reacting the activated cyclodextrin with an appropriate quantity of 1,4-butane sultone;
c. adjusting pH of the reaction mass to 6-6.5 using aqueous hydrochloric acid and removing coloured impurities by the process comprising treatment with neutral charcoal, stirring and filtering the reaction mass under vacuum through Hyflo at 25-30° C.;
d. removing the unreacted 1,4-butane sultone by a process comprising washing the reaction mass with an organic solvent and separating the aqueous and organic layers followed by ultrafiltration by employing 1.0 KD membrane;
e. treating the retentate with neutral charcoal and again passing through ultrafiltration using 10 KD membrane system to eliminate bacterial endotoxins; and
f. the aqueous solution of sulfobutylether beta cyclodextrin sodium was freeze dried by lyophilization to produce sulfobutylether beta cyclodextrin sodium (I);

wherein the characteristics of the obtained sulfobutylether beta cyclodextrin sodium (I) comprises of:
i. UV absorbance in the range of 245 nm to 270 nm and 320 nm to 350 nm at 500 mg/mL concentration is greater than 0.5 A. U,
ii. UV absorbance in the range of 245 nm to 270 nm and 320 nm to 350 nm at 300 mg/mL concentration is greater than 1.0 A. U,
iii. Bulk density greater than 0.67 g/cm$^3$,
iv. Tap density greater than 0.76 g/cm$^3$,
v. 1,4-butane sultone content less than 0.5 ppm or
vi. having BET (Bacterial endotoxins) less than 10 IU/g.

The present invention is schematically represented as:

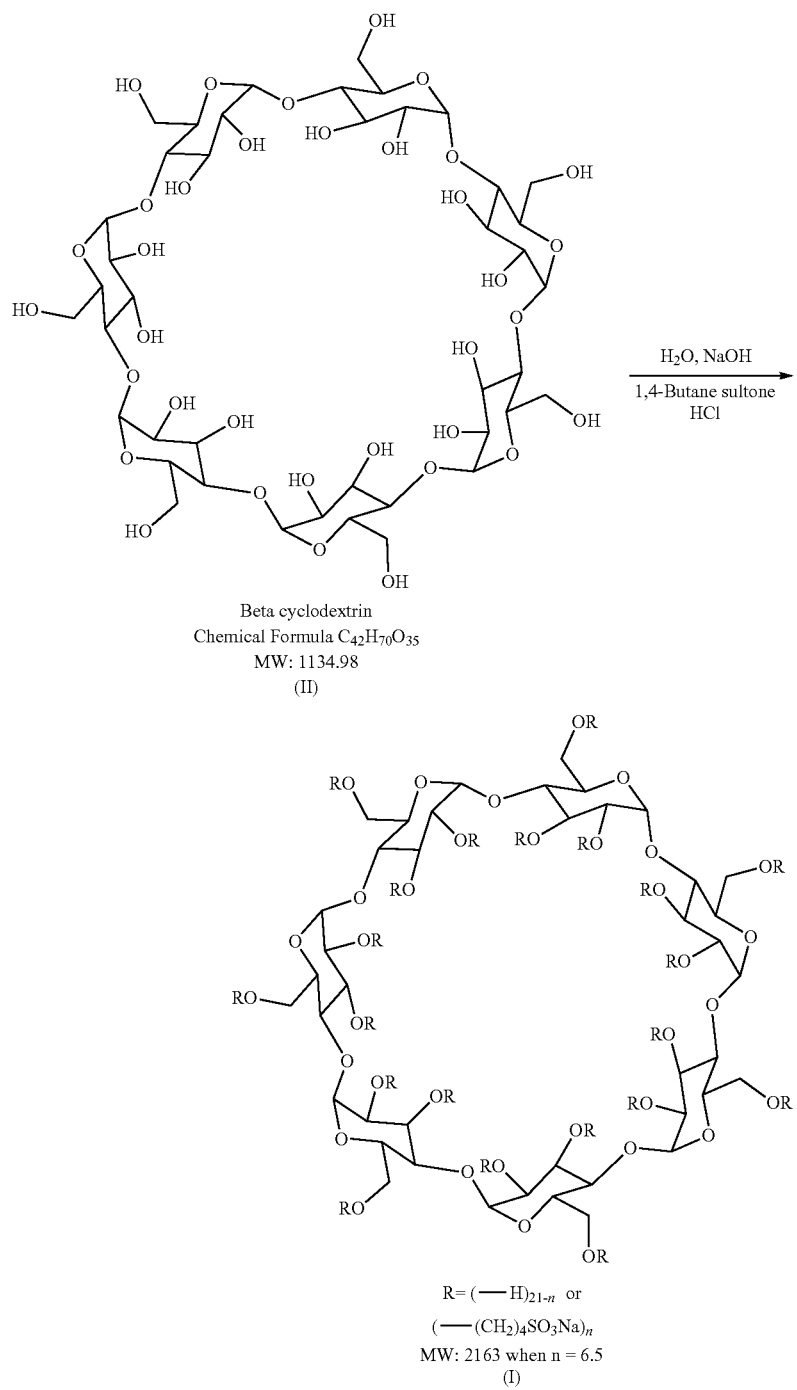

In step-a), activated beta cyclodextrin is prepared by adding beta cyclodextrin in portions to an aqueous solution of base at temperature ranging from 30-70° C., preferably at 45-55° C. Suitable base includes sodium hydroxide, sodium bicarbonate, and combination thereof. The base can be employed in quantities ranging from 0.3 to 0.5 equivalents with respect to beta cyclodextrin.

In step-b), 1,4-Butane sultone is added drop wise to the activated aqueous solution of the beta cyclodextrin. The addition of butane sultone is carried out at temperature between 60-90° C., preferably at 70-80° C. The 1,4-butane sultone alkylating agent can be used in quantities ranging from 7-10 equivalents, preferably 7-9.5 equivalents, most preferably 8-9.5 equivalents. The reaction is maintained till the residual unreacted cyclodextrin is less than 0.5% by weight, preferably less than 0.05% by weight.

In step-c), reaction mass is cooled to room temperature and the pH is adjusted to 5.5-7.0 with aqueous hydrochloric acid, preferably to pH 6.0-6.5. The colored impurities of the reaction can be removed by treating with neutral charcoal.

In step-d), the unreacted butane sultone is removed by washing the aqueous reaction mass with an organic solvent. Suitable organic solvents include dichloromethane, ethyl acetate, methylene chloride, diethyl ether, methyl tert-butyl ether, preferably methylenechloride. Multiple washings may be required to remove the 1,4-butane sultone to an extent of less than 0.5 ppm in the final cyclodextrin derivative.

The prior art process involves quenching of the residual sultone by treating the total reaction mass with excess base at higher temperature that ultimately results in impurities like hydroxyl butane-1-sulfonic acid, bis(4-sulfobutyl) ether and other ring opening polymerization impurities. Usage of excessive base and high temperatures as described in the prior art for the quenching of 1,4-butane sultone would also lead to coloration of the reaction mass. Thus the removal of residual 1,4-butane sultone by washing with organic solvent provides advantage over the prior art process and also renders the process simple and industrially viable.

The crude aqueous sulfobutylether beta cyclodextrin sodium obtained is further purified by ultrafiltration process using 700 Dalton to 1.3 KD membrane, preferably 1 KD membrane. The purified aqueous sulfobutylether beta cyclodextrin sodium (SBECD) solution is concentrated by vacuum distillation to an extent of 15-30% solution (w/v) of the product.

In step-e), the concentrated aqueous sulfobutylether beta cyclodextrin sodium solution (15-30% w/v) is passed through a 10 KD membrane ultrafiltration and the permeate is collected. The obtained permeate solution is exceptionally low in endotoxin levels or free of bacterial endotoxins.

Bacterial endotoxins are usual contaminants when products are isolated from aqueous medium. Endotoxins can be considered as temperature and pH stable, rendering their removal as one of the most challenging task in obtaining the pure sulfobutylether beta cyclodextrin sodium on commercial scale. So the present inventors report a novel purification procedure, which forms a part of the embodiment, wherein the SBECD solution obtained by ultrafiltration process using 700 Dalton to 1.3 KD membrane, preferably 1 KD membrane is concentrated to 15-30% (w/v) and is then subjected to ultrafiltration using 10 KD membrane resulting in sulfobutylether beta cyclodextrin sodium, which has substantially lesser BET, less than 35 IU/g of BET, preferably less than 10 IU/g of BET or more preferably free of bacterial endotoxins.

In step-f), the aqueous solution of sulfobutylether beta cyclodextrin sodium obtained in step-f is lyophilized to give amorphous form of sulfobutylether beta cyclodextrin sodium (I).

The characteristics of the final compound of sulfobutylether beta cyclodextrin sodium (I) (SBECD) obtained from the present process comprises of:

i. UV absorbance in the range of 245 nm to 270 nmand 320 nm to 350 nm at 500 mg/mL concentration is greater than 0.5 A. U,
ii. UV absorbance in the range of 245 nm to 270 nmand 320 nm to 350 nm at 300 mg/mL concentration is greater than 1.0 A. U,
iii. Bulk density greater than 0.67 g/cm$^3$,
iv. Tap density greater than 0.76 g/cm$^3$,
v. 1,4-butane sultone content less than 0.5 ppm or
vi. BET (Bacterial endotoxins) less than 10 IU/g In some embodiment of the invention, there is provided a process for the preparation of sulfobutylether beta cyclodextrin sodium (I) having and average degree of substitution of 6.2 to 6.9, preferably 6.5.

In some other embodiment of the invention, there is provided a process for preparing sulfobutylether beta cyclodextrin sodium (I) having bacterial endotoxins less than 10 IU/g, the said process comprising the steps of:

a. purifying crude aqueous sulfobutylether beta cyclodextrin sodium by ultrafiltration using 700 Dalton to 1.0 KD membrane;
b. concentrating the aqueous layer to 15-30% of (w/v) by vacuum distillation;
c. passing the concentrated aqueous sulfobutylether beta cyclodextrin sodium through 10 KD membrane in ultrafiltration; and
d. lyophilization of aqueous sulfobutylether beta cyclodextrin sodium (I) obtained in step (c) to obtain sulfobutylether beta cyclodextrin sodium (I) having bacterial endotoxins less than 10 IU/g.

Sulfobutylether beta cyclodextrin sodium crude obtained from any known synthetic procedures of the prior art can be purified to remove bacterial endotoxins (BET) by employing the reaction stages of d) to f).

In one aspect of the invention, the sulfobutylether beta cyclodextrin sodium produced by the invented method is amorphous powder, which is characterized by the X-Ray powder diffraction method as shown in FIG. 1.

In conclusion, the authors have disclosed an improved industrial scale process for the synthesis of sulfobutylether beta cyclodextrin sodium, which has substantially lesser amounts of bacterial endotoxins.

The following examples further illustrate the present invention, but should not be construed in any way as to limit its scope.

EXAMPLES

Preparation of Sulfobutylether Beta Cyclodextrin Sodium (I)

200 g of sodium hydroxide was slowly added to 800 mL to DM water at 25-30° C. and heated to 40-50° C. 50 g (0.44 moles) of Beta cyclodextrin (II) was added slowly to the above solution at 40-50° C. over a period of 5-10 minutes (portion wise) and the reaction mixture was stirred for 10-15 minutes. The temperature was slowly raised to 75-80° C. and 509.27 g of 1,4-Butane sultone was added drop wise over a period of 60-90 minutes.

The above reaction mixture was heated to 80-85° C. for 6-7 hrs., cooled to 25-30° C. followed by adjusting the pH of reaction mass between 6.0-6.5 with ~43 mL of concentrated hydrochloric acid. The colored impurities were removed by treating the above mixture with 50 g of neutral charcoal (Norit CN1), stirring for 15-20 minutes and filtering the reaction mass under vacuum through Hyflo. The filtrate so obtained was treated with dichloromethane, stirred, the layers separated and the process repeated. The pH of the aqueous layer was maintained between 4.5-6.0 using 10% sodium hydroxide or 10% aqueous hydrochloric acid and 1,4-Butane sultone content was not more than 0.5 ppm.

The aqueous layer was further filtered through 1 KD ultrafiltration membrane, volume adjusted using DM water and the filtration is repeated again, there after the retentate was treated with neutral charcoal and passed through Hyflo at 25-30° C., concentrated the aqueous sulfobutylether beta cyclodextrin sodium solution to 15-30% (w/v), then passed through 10 KD ultrafiltration membrane system, followed by passing through 0.2-micron system and dried completely (moisture content should not be more than 10.0%) through Lyophilization, then milled to yield 250-275 g of pure amorphous sulfobutylether beta cyclodextrin sodium (I) with 26-29% yield.
 a. Bulk density: 0.81 g/cm$^3$
 b. Tap density: 1.07 g/cm$^3$
 c. 1,4-Butane sultone content: <0.5 ppm
 d. BET: less than 10 IU/g While the present disclosure has been illustrated and described with respect to a particular embodiment thereof, it should be appreciated by those of ordinary skill in the art that various modifications to this disclosure may be made without departing from the spirit and scope of the present disclosure.

What is claimed is:

1. A process for the preparation of pure sulfobutylether beta cyclodextrin sodium of formula (I), obtained by the process comprising the steps of:
 purifying crude aqueous sulfobutylether beta cyclodextrin sodium by ultrafiltration using 700 Dalton to 1.0 KD membrane,
 concentrating the aqueous layer to 15-30% of (w/v) under vacuum, and
 passing the concentrated aqueous sulfobutylether beta cyclodextrin sodium through 10 KD membrane in ultrafiltration method, wherein pure sulfobutylether beta cyclodextrin sodium of formula (I) obtained by the process is characterized by one or more of the following:
 I. 1,4-butane sultone content less than 0.5 ppm; and
 II. having BET (Bacterial endotoxins) less than 10 IU/g.

2. A process for preparing sulfobutylether beta cyclodextrin sodium of formula (I) the said process comprising the steps of:
 a) treating beta-cyclodextrin with an aqueous base to form activated beta-cyclodextrin;
 b) reacting the activated beta cyclodextrin with 1,4-butane sultone;
 c) adjusting pH of the reaction mass to 6-6.5 using aqueous hydrochloric acid;
 d) removing the unreacted 1,4-butane sultone by washing the reaction mass with an organic solvent and separating the aqueous and organic layers followed by ultrafiltration by employing 1.0 KD membrane, and again passing through ultrafiltration using 10 KD membrane; and
 e) freeze drying the sulfobutylether beta cyclodextrin sodium (I) by lyophilization to obtain sulfobutylether beta cyclodextrin sodium (I) having 1,4-butane sultone content less than 0.5 ppm.

3. The process as claimed in claim 2, wherein the aqueous base used in step a) is selected from sodium hydroxide or sodium bicarbonate.

4. The process as claimed in claim 2, wherein the 1,4-butane sultone quantity used in step b) is in between 7-9.5 equivalents.

5. The process as claimed in claim 2, wherein the sulfobutylether beta cyclodextrin sodium (I) comprises less than 0.5% (w/w) of unreacted beta cyclodextrin.

6. The process as claimed in claim 2, wherein organic solvent used in step d) is selected from the group comprising of dichloromethane, ethyl acetate, methylene chloride, diethyl ether and methyl tertiary butyl ether.

7. The process as claimed in claim 2, wherein the sulfobutylether beta cyclodextrin sodium (I) has average degree of substitution of 6.2 to 6.9.

8. A process for preparing sulfobutylether beta cyclodextrin sodium of formula (I) having bacterial endotoxins less than 10 IU/g,

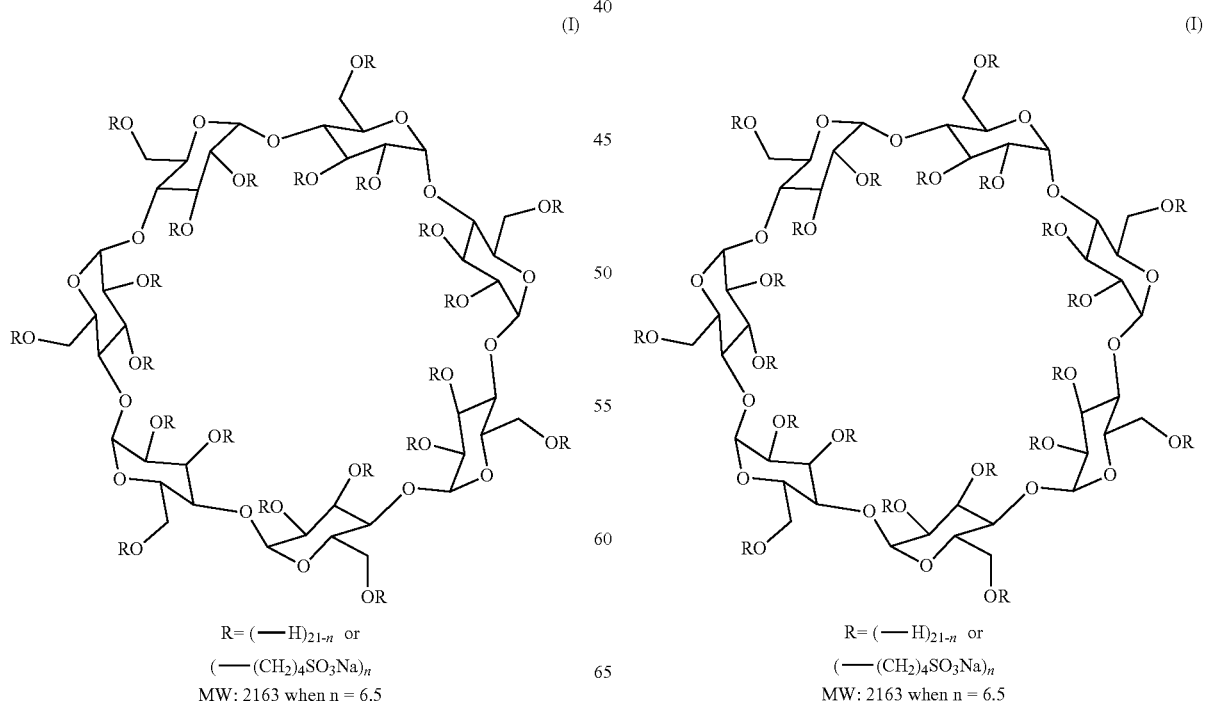

the said process comprising the steps of:
  a. purifying crude aqueous sulfobutylether beta cyclodextrin sodium by ultrafiltration using 700 Dalton to 1.0 KD membrane;
  b. concentrating the aqueous layer to 15-30% of (w/v) under vacuum;
  c. passing the concentrated aqueous sulfobutylether beta cyclodextrin sodium through 10 KD membrane in ultrafiltration; and
  d. lyophilization of aqueous sulfobutylether beta cyclodextrin sodium obtained in step (c) to obtain sulfobutylether beta cyclodextrin sodium (I) having bacterial endotoxins less than 10 IU/g.

9. The process as claimed in claim 2, wherein the sulfobutylether beta cyclodextrin sodium (I) obtained is an amorphous powder.

* * * * *